United States Patent [19]
Chen

[11] Patent Number: 5,336,233
[45] Date of Patent: Aug. 9, 1994

[54] ANASTOMOTIC DEVICE

[76] Inventor: Fusen H. Chen, 12 Vernon La., Thompson, Conn. 06277

[21] Appl. No.: 37,399

[22] Filed: Mar. 26, 1993

Related U.S. Application Data

[63] Continuation-in-part of Ser. No. 902,210, Jun. 22, 1992, Pat. No. 5,250,057, which is a continuation-in-part of Ser. No. 735,950, Jul. 25, 1991, Pat. No. 5,123,908, which is a continuation-in-part of Ser. No. 629,608, Dec. 18, 1990, Pat. No. 5,089,008, which is a continuation-in-part of Ser. No. 472,209, Jan. 26, 1990, Pat. No. 4,997,439, which is a continuation-in-part of Ser. No. 303,326, Jan. 26, 1989, Pat. No. 4,930,502.

[51] Int. Cl.⁵ .............................................. A61B 17/00
[52] U.S. Cl. ...................................... 606/153; 606/154
[58] Field of Search ...................... 606/153, 220, 154

[56] References Cited
U.S. PATENT DOCUMENTS

| | | | |
|---|---|---|---|
| 2,638,901 | 5/1953 | Sugarbaker | 606/153 |
| 3,254,650 | 6/1966 | Collito | 606/153 |
| 3,316,914 | 5/1967 | Collito | 606/153 |
| 4,294,255 | 10/1981 | Geroc | 606/153 |
| 4,627,437 | 12/1986 | Bedi et al. | 606/220 |
| 4,747,407 | 5/1988 | Liu et al. | 606/153 |
| 4,917,090 | 4/1990 | Berggren et al. | 606/153 |

Primary Examiner—Stephen C. Pellegrino
Assistant Examiner—Gary Jackson
Attorney, Agent, or Firm—Morris Kaplan

[57] ABSTRACT

An annuli pair provide an anastomotic clamp. Each operatively associated, opposed face of the annuli pair has a plurality of serrated impaling pins and tang-containing apertures that lockingly associated in assembly for anastomosis. The back surface of each annulus is substantially recessed about each aperture whereby to accommodate all or substantially all of the impaling pin extending past the locking tang. The annuli have alignment indicator means integral therewith to facilitate handling and assembly.

2 Claims, 4 Drawing Sheets

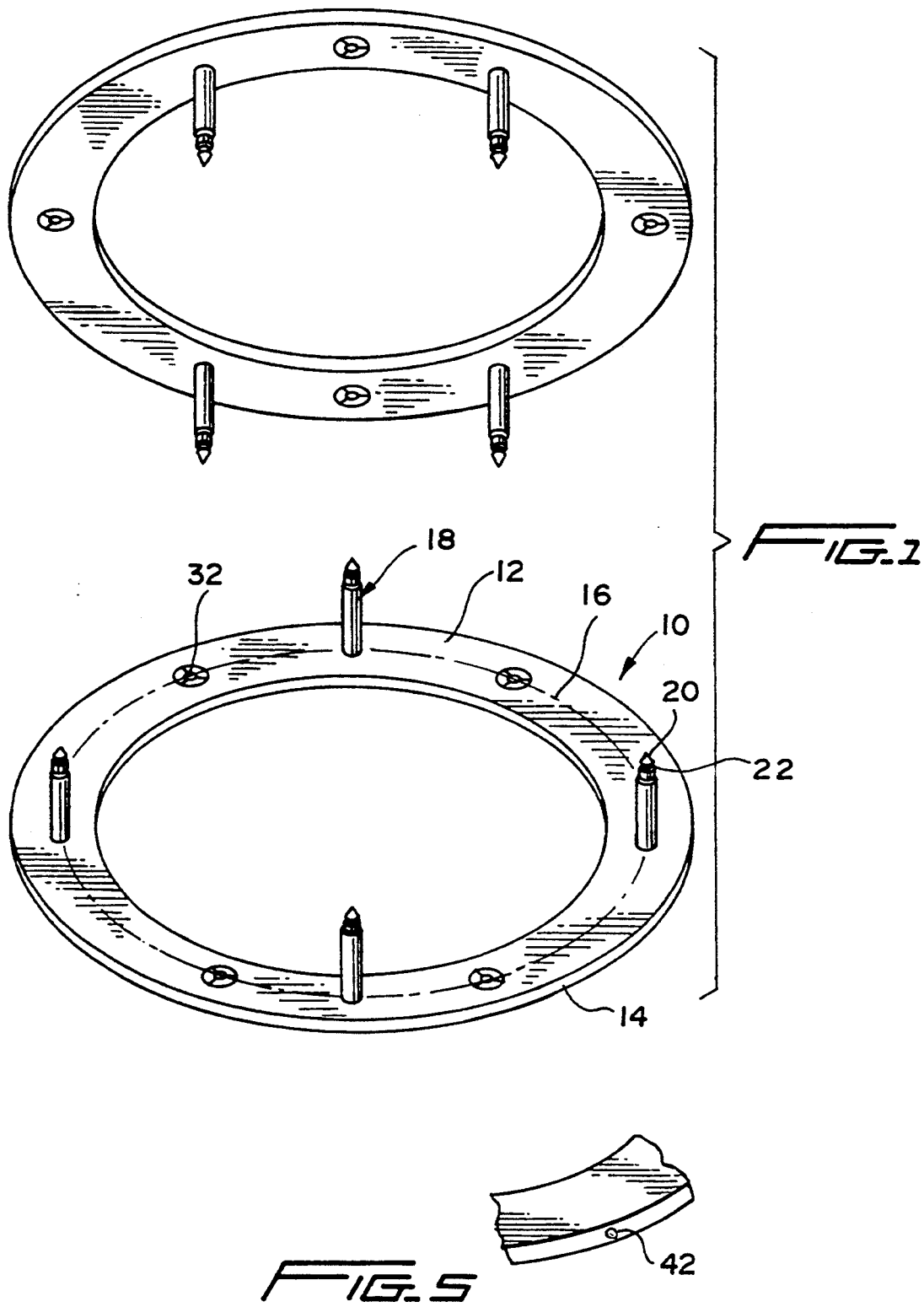

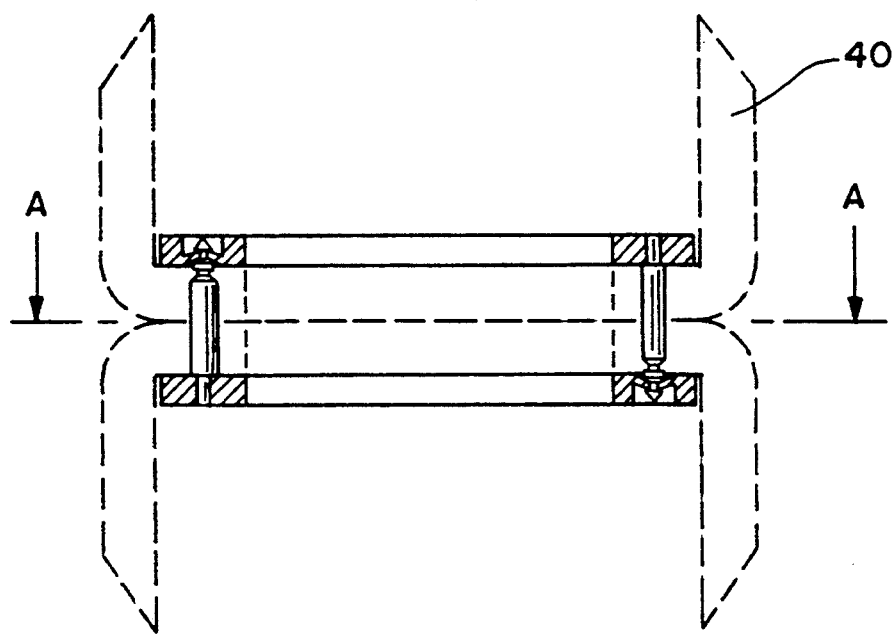
FIG_2
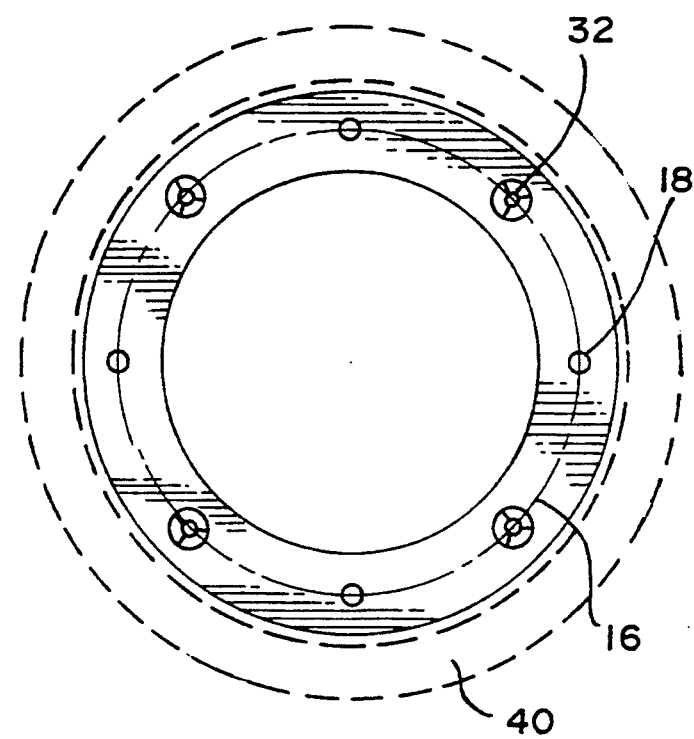
FIG_3

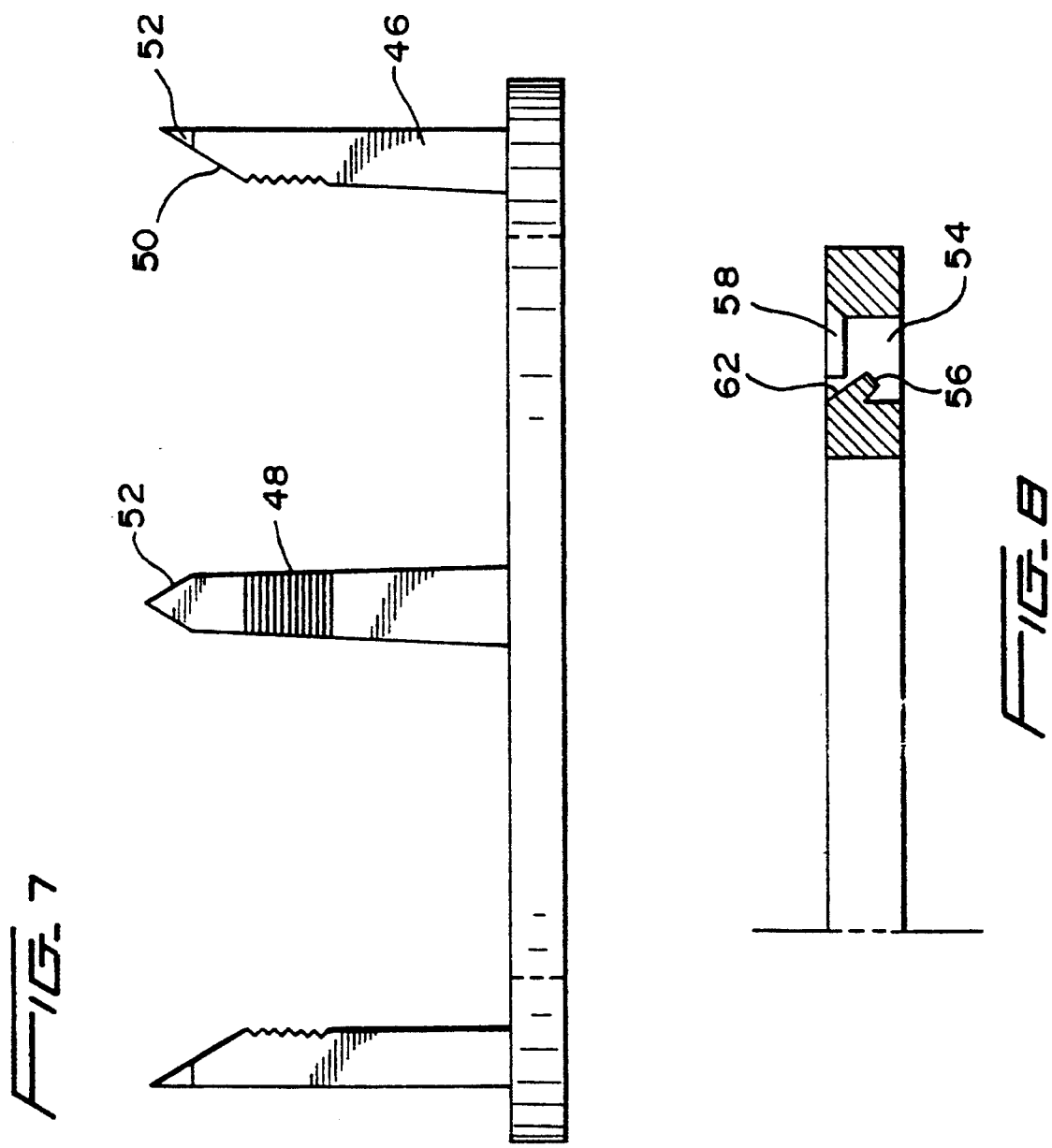

ANASTOMOTIC DEVICE

CROSS-REFERENCE TO RELATED APPLICATIONS

This application is a continuation-in-part of copending application Ser. No. 07/902,210, filed Jun. 22, 1992, now U.S. Pat. No. 5,250,057, which a continuation-in-part of application Ser. No. 07/735,950, filed Jul. 25, 1991, now U.S. Pat. No. 5,123,908, which is a continuation-in-part of application Ser. No. 07/629,608, filed Dec. 18, 1990, now U.S. Pat. No. 5,089,008, which is a continuation-in-part of application Ser. No. 07/472,209, filed Jan. 26, 1990, now U.S. Pat. No. 4,997,439, which is a continuation-in-part of application Ser. No. 07/303,326, filed Jan. 26, 1989, now U.S. Pat. No. 4,930,502.

TECHNICAL FIELD

The present invention relates to the surgical joining of tubular structures.

BACKGROUND OF THE INVENTION

Anastomosis, both vascular and recto-colic, is a well-known art that can be practiced by the use of mechanical devices and without resort to sewing sutures. For optimum results in the practice of the art, it is necessary to maintain patency of the lumina without undue stress of the lumen wall that could lead to tearing, spasm, and thrombosis and to maintain patency and minimize surgical time by reliance on anastomotic means that are minimal in bulk, simplified in structure, do not require sophisticated handling, and can be quickly assembled in surgery.

In these regards, as the following U.S. patents illustrate, the known art is wanting.

Zack, U.S. Pat. No. 2,453,056, performs a 180° eversion of a substantial portion of a lumen wall about a tubular member and then uses two annular rings to separately clamp respective lumen walls to such member.

The recto-colic clamp of Sugarbaker, U.S. Pat. No. 2,638,901, is relatively ponderous, awkward to use, and requires threaded elements to maintain clamping.

Collito, U.S. Pat. No. 3,254,650, in a more convenient to use of the disclosed species, requires that impaling nails be clinched.

Schomacher, U.S. Pat. No. 4,233,981, complicates assembly in surgery by use of separate impaling elements and clamping means comprised of threaded members and separate nut means therewith.

Geroc, U.S. Pat. No. 4,294,255, discloses an anastomotic device requiring a pair of relatively sophisticated ring structures and separate pin means accommodated in each ring.

Daniel, U.S. Pat. No. 4,523,592, discloses barbed impaling elements that extend from opposed faces of associated ring elements and are adapted to each couple with an open-ended slot structure in the opposed face. The structure does not offer positive fixing since the slots are open-ended, and the barbs may slide free upon further handling, stress, or poor assembly.

Schenk et al., in a first anastomotic device disclosure, U.S. Pat. No. 4,624,255, requires use of a pneumatic means and, in a second disclosure, U.S. Pat. No. 4,693,249, complicates assembly by requiring manipulation of a split ring and the structurally awkward use of impaling means that extend normal to the edge surface of the ring and through unsupported lumenal wall sections, whereby the wall is relatively more apt to tear.

Liu et al., U.S. Pat. No. 4,747,407, requires sophistical handling and the use of clinching tools.

SUMMARY OF THE INVENTION

The present invention is drawn to an anastomotic device that is ideally comprised of a pair of identically simplified parts that are of minimal bulk, inexpensive to manufacture, easily and quickly assembled, and, when assembled, will positively fix and adjustably clamp the anastomosed walls therebetween.

It is an object of the invention that lumen wall-impaling pins extend normal to, and from, opposed planar walls of annular members and that each pin lock into a respective aperture disposed in an intermediate section of the associated opposed wall.

It is a further object of the invention that the operatively associated pin and aperture structures be configured to provide positive, adjustable locking means.

It is another object of the invention to provide alignment indicator means that are integral with the annular members.

For a more fully developed presentation of the invention and a preferred embodiment thereof, reference is made to the following descriptive matter, attached drawings, and claims.

BRIEF DESCRIPTION OF THE DRAWINGS

FIG. 1 is an exploded perspective view of a first embodiment of the invention and shows the inner faces of annuli to be operatively associated.

FIG. 2 is a diametric partial cross-section of the first embodiment in functional association with anastomosed lumen walls shown in broken lines.

FIG. 3 is a plan view taken on cut lines A—A of FIG. 2.

FIG. 5 is a partial perspective view of an annulus having an alignment element.

FIG. 7 is a partial elevational view of FIG. 6.

FIG. 8 is a sectional view taken on cut line B—B of FIG. 6.

DETAILED DESCRIPTION OF THE INVENTION

Figure 4:
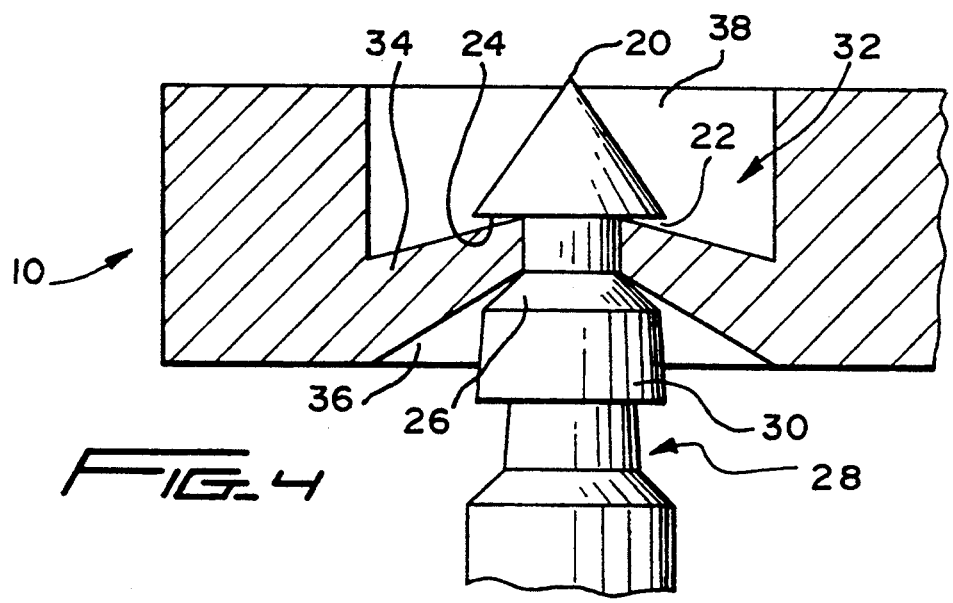
FIG. 4 is an enlargement of a partial sectional view of FIG. 2.

Referring to the drawings which illustrate preferred embodiments of the invention and wherein like numerals indicate like elements of structure, there is shown in FIGS. 1–4 a pair of annuli 10 which are of identical structure for purposes of minimal cost of manufacture, expediency of assembly, and minimizing surgical time. Each annulus 10 has generally planar faces 12, is of relatively narrow edge thickness 14, and is severely limited in radial dimension, as dictated by the properties of the material of fabrication whereby to limit bulk, provide a proper seal for anastomosis, and maintain patency of the lumen.

At an equal radial circumference 16 of each opposed face of the annuli is disposed equispaced pins 18 that extend normal to the respective associated face 12. Each pin 18 is pointed at its free end 20 and, at a distal section thereof, has serrations or grooves 22 about the periphery thereof. The pin section sidewall 24 of the groove is at least planar but may be undercut and is normal to the pin axis.

Preferably, the inner sidewall 26 of the groove is canted inwardly towards the groove opening, and a like second groove 28 is provided at said distal pin section.

As illustrated in all of the figures of drawing, and especially in FIG. 4, the dimensions of structure are exaggerated for purposes of clarity, but it will be understood that the grooves 22, 28 are very close to one another; and, for ease of manipulation, the diameter of the peripheral wall 30 that separates the grooves is of a slightly lesser diameter with respect to surface 24 and, as illustrated, is slightly tapered. The proximal wall 26 of the groove is tapered whereby in each case to facilitate adjustment and for the proper interfit of the parts.

Alternating with said pins on circumference 16 of the opposed annuli faces, and equispaced as are the pins, are apertures 32 that are each defined by a plurality of relatively thin, flexible tang elements 34 that are configured to form a beveled guide surface 36 in the respective front annuli faces to be operatively associated. The backside of each annulus is recessed 38 to the depth of said flexible tangs. As shown in FIG. 4, the pin structure and that of the recess, aperture, and tangs are configured to lockingly operatively associate for anastomosis, as illustrated with the lumen walls 40, shown in broken lines in FIG. 2.

The illustrated structure of FIG. 4 is highly exaggerated for purposes of clarity. In matter of fact, the locked-in end structure of the pin is either substantially or completely within the recess, no matter which groove is selected for purposes of adjustment of pressure.

FIG. 2 illustrates the annuli disposed within the lumen walls but, depending on the anatomical circumstances, may be associated externally of such walls. In practice of the illustrated instance, a first annulus is inserted within a first lumen wall section to be anastomosed; and the end section of the lumen wall is partially everted and impaled on the outwardly extending pins, as shown in FIG. 2, care being taken that the lumen end wall does not extend beyond the annulus inner circumference so as to impede flow. The sequence is repeated with respect to the second annulus and the lumen wall section to be anastomosed, the second annulus being oriented with the second lumen wall section so that each of the opposed sets of impaling pins will be in substantial alignment with the respective opposed sets of tang-defining apertures. The annuli, thus mounted, are then operatively associated to lock each pin in a respective opposed tang structure whereby to effect anastomosis.

It is important to note that surgical time is reduced because the composite device is of identical parts and because such parts are quickly and easily assembled with respective lumen walls and each other, that the device maintains patency without excessive bulkiness, requires relatively little lumen wall eversion, easily adjusts for clamping pressure, and that the impaled areas of the lumen walls are supported between the clamping walls to thus inhibit stress-induced tearing.

To further facilitate assembly of the device, its parts are each made integral with alignment indicator means. FIG. 5 illustrates one such indicator means as a needle-like element 42 projecting normal to an edge of the annulus. The indicator element is soft, flexible, and easily bent and distorted by a lumen wall.

It is obvious that the indicator element may be located on a internal edge wall and that the alignment purpose would be served equally well by a small nub or other configuration such as a slight groove or a small faceted edge section.

Figure 6:
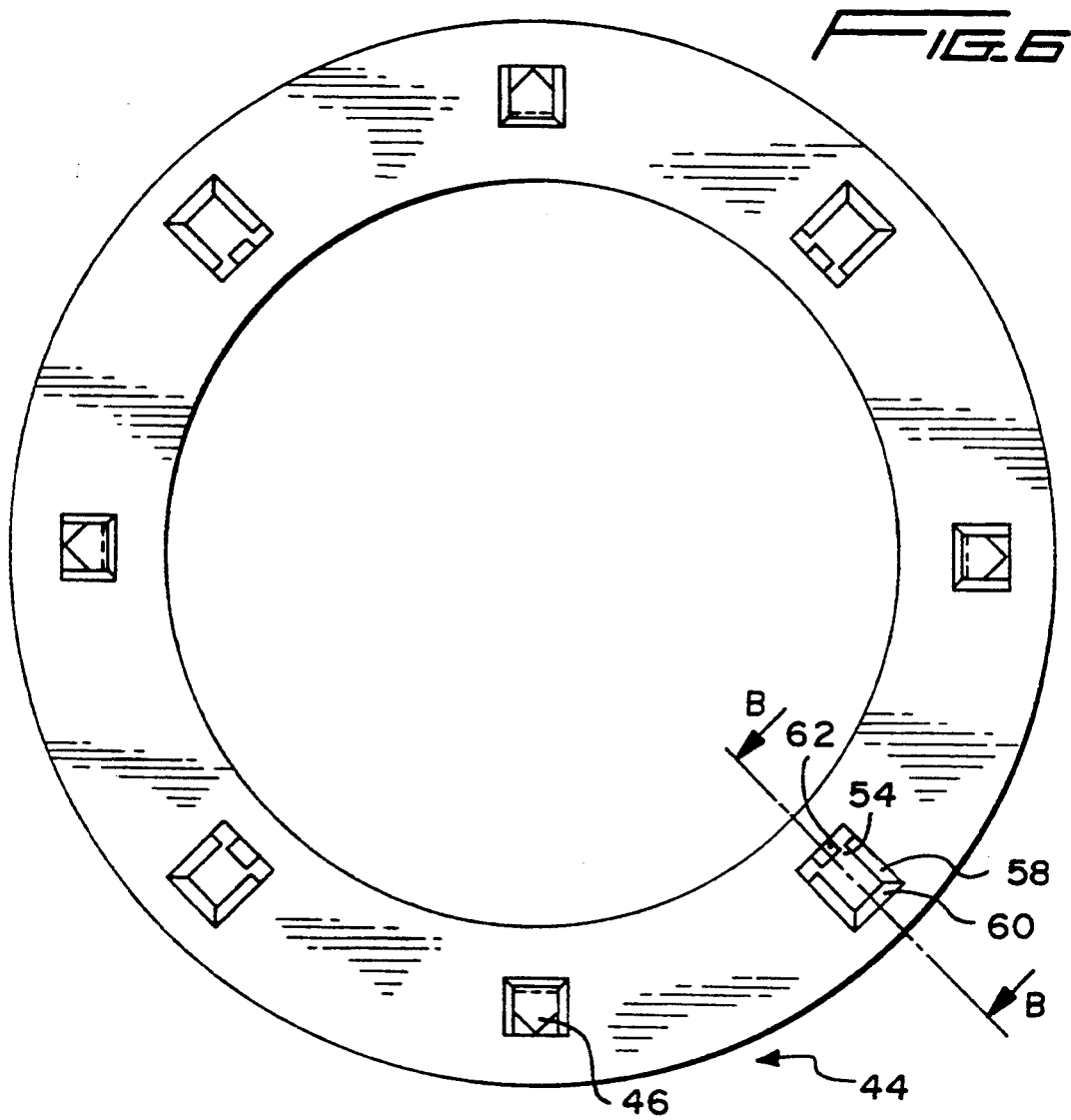
FIG. 6 is a plan view of an inner face of an annulus of a second embodiment of the invention.

FIGS. 6–8 illustrate a second and preferred species of the invention, wherein the annuli pair are again of duplicate structure and differ from that illustrated in FIGS. 1–5 only as to configuration of the impaling pins and aperture-defining structure in which the pins are locked.

Only a single annulus 44 is illustrated. The impaling pins 46 are generally rectangular in cross-section and slightly tapered in the elongate direction, e.g., 2°. Only the pins' inner face is serrated 48 at an end section. The pin is tapered 50 from its endmost serration which with tapered pin sidewalls 52 form a pointed end.

Apertures 54 generally conform to the associated pin cross-sectional configuration except that from one wall of the aperture, a single tang 56 extends. The aperture-defining walls are beveled at 58, 60 and, together with a beveled tang surface 62, form guide means for the associated impaling pin.

It is pointed out that the impaling pins 46 may be variously configured in cross-section and that the width of the serration bearing wall may be of any width as long as effecting a locking relationship with the single tang element relied on.

The materials of fabrication are compatible with human tissue and, as is known in the art, may be of an absorbable polyglycolic or polyactic material.

The embodiments shown and described are only illustrative of the present invention and are not to be construed as delimitive thereof since, once apprised of the invention, changes in structure would be readily apparent to one skilled in the art. Hence, the present invention includes all modifications of structure encompassed within the spirit and scope of the following claims.

I claim:

1. An anastomotic device, especially adapted for anastomosis by intraluminal disposition and without the intervention of additional mechanical holding or clamping means, comprising:
    a pair of annuli;
    each annulus of the pair being a relatively thin, flat ring having a plurality of impaling pins integral therewith and extending circumferentially and normally from one face thereof;
    each pin being pointed at its end to facilitate an impaling function and being transversely serrated at an end section remote from the ring;
    each said ring having a plurality of apertures therethrough, said pins and apertures circumferentially alternating with one another;
    said one face of each annulus being beveled about each said aperture for a pin guiding function;
    each aperture having therein a relatively thin flexible tang that is an extension from the inner periphery of the aperture defining annulus structure;
    an alignment indicator element integral with and extending from a periphery of each said ring; and
    the parts being configured and dimensioned whereby with the parts to be anastomosed each mounted on and about a respective ring member and the indicator elements aligned, the rings are operatively associated with one another for anastomosis whereby each pin is guided and received within an opposed operatively associated aperture, with the tang of said associated aperture lockingly engaged with a said serration, and said anastomosed parts are claimed between operatively associated flat surfaces of said annuli.

2. An anastomotic device as in claim 1, wherein each alignment indicator element is a simple nub configuration.

* * * * *